US011717234B2

(12) United States Patent
Roberts et al.

(10) Patent No.: US 11,717,234 B2
(45) Date of Patent: *Aug. 8, 2023

(54) FORECASTING NEONATAL VITALITY

(71) Applicant: CERNER INNOVATION, INC., Kansas City, KS (US)

(72) Inventors: Andrew Roberts, Overland Park, KS (US); Sasanka Are, Topeka, KS (US); Jeffrey W. Wall, Overland Park, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 127 days.

This patent is subject to a terminal disclaimer.

(21) Appl. No.: 17/349,011

(22) Filed: Jun. 16, 2021

(65) Prior Publication Data
US 2021/0307703 A1 Oct. 7, 2021

Related U.S. Application Data

(63) Continuation of application No. 16/154,480, filed on Oct. 8, 2018, now Pat. No. 11,045,148.

(60) Provisional application No. 62/569,546, filed on Oct. 8, 2017.

(51) Int. Cl.
*A61B 5/00* (2006.01)
*A61B 5/024* (2006.01)
(Continued)

(52) U.S. Cl.
CPC .......... *A61B 5/7275* (2013.01); *A61B 5/0011* (2013.01); *A61B 5/02405* (2013.01);
(Continued)

(58) Field of Classification Search
CPC . A61B 5/7275; A61B 5/0011; A61B 5/02405; A61B 5/02411; A61B 5/150038;
(Continued)

(56) References Cited

U.S. PATENT DOCUMENTS

2002/0193670 A1  12/2002  Garfield et al.
2007/0233203 A1  10/2007  Euliano et al.
(Continued)

OTHER PUBLICATIONS

Abry et al., "Hurst Exponent IntraPartum Fetal Heart Rate: Impact of Decelerations", Proceedings of the IEEE Symposium on Computer-Based Medical Systems, Jan. 2013, 7 pages.
(Continued)

*Primary Examiner* — Eric F Winakur
*Assistant Examiner* — Abid A Mustansir
(74) *Attorney, Agent, or Firm* — Invoke

(57) ABSTRACT

A decision support tool is provided for predicting the neonatal vitality scores of a fetus during delivery, the scores being an indicator of future health for the infant anticipated to be born within a future time interval, measured as time to birth. The predicted neonatal vitality score is determined from measurements of physiological variables monitored during labor, such as uterine activity and fetal heart rate. Fetal heart rate variability and patterns may be detected and computed using the monitored physiological variables, and neonatal vitality scores may be predicted based, at least in part, on the variability metrics and fetal heart rate patterns. Scores may be predicted for different delivery methods, such as vaginal delivery or cesarean delivery, for different time-to-birth intervals. In this way, these scores may be used for decision support for care plans during labor, such as increased monitoring and/or modifying the delivery type.

31 Claims, 9 Drawing Sheets

(51) Int. Cl.
  *A61B 5/15* (2006.01)
  *A61B 5/145* (2006.01)
  *A61B 5/08* (2006.01)
  *A61B 5/021* (2006.01)

(52) U.S. Cl.
  CPC .... *A61B 5/02411* (2013.01); *A61B 5/150038* (2013.01); *A61B 5/4356* (2013.01); *A61B 5/4362* (2013.01); *A61B 5/7203* (2013.01); *A61B 5/0022* (2013.01); *A61B 5/021* (2013.01); *A61B 5/024* (2013.01); *A61B 5/0816* (2013.01); *A61B 5/14539* (2013.01); *A61B 5/7267* (2013.01); *A61B 5/746* (2013.01)

(58) Field of Classification Search
  CPC ... A61B 5/4356; A61B 5/4362; A61B 5/7203; A61B 5/0022; A61B 5/021; A61B 5/024; A61B 5/0816; A61B 5/14539; A61B 5/7267; A61B 5/746; G16H 50/30
  See application file for complete search history.

(56) References Cited

U.S. PATENT DOCUMENTS

| | | |
|---|---|---|
| 2009/0299212 A1 | 12/2009 | Principe et al. |
| 2011/0192398 A1 | 8/2011 | Euliano et al. |
| 2019/0133536 A1 | 5/2019 | Roberts et al. |
| 2019/0274618 A1* | 9/2019 | Evans ................. A61B 5/4362 |
| 2020/0196958 A1 | 6/2020 | Penders et al. |

OTHER PUBLICATIONS

Ayres-De-Campos et al., "Prediction of neonatal state by computer analysis of fetal heart rate tracings: the antepartum arm of the SisPorto® multicentre validation study", European Journal of Obsterics & Gynecology and Reproductive Biology, 2005, pp. 52-60.

Georgoulas et al., "Predicting the Risk of Metabolic Acidosis for Newborns Based on Fetal Heart Rate Signal Classification Using Support Vector Machines", IEEE Transactions on Biomedical Engineering, vol. 53, No. 5, May 2006, pp. 875-884.

Parer, Juliant, "A Framework for Standardized Management of Intrapartum Fetal Heart Rate Patterns", American Journal of Obstetrics and Gynecology, Jul. 2007, pp. 26.e1-26.e6.

Rotariu et al., "Spectral Analysis of Fetal Heart Rate Variability Associated with Fetal Acidosis and Base Deficit Values", 12th International Conference on Development and Application Systems, Suceava, Romania, May 15-17, 2014, pp. 210-213.

Non-Final Office Action received for U.S. Appl. No. 16/154,495, dated Mar. 25, 2022, 15 pages.

Final Office Action received for U.S. Appl. No. 16/154,495, dated Aug. 16, 2022, 15 pages.

Non-Final Office Action received for U.S. Appl. No. 16/154,491, dated Jun. 23, 2022, 13 pages.

* cited by examiner

FORECASTING NEONATAL VITALITY

CROSS-REFERENCE TO RELATED APPLICATIONS

This application is a continuation of U.S. application Ser. No. 16/154,480, titled "FORECASTING NEONATAL VITALITY" and filed on Oct. 8, 2018, which claims the benefit of U.S. Provisional Application No. 62/569,546 titled "FORECASTING NEONATAL VITALITY," filed on Oct. 8, 2017, which is hereby expressly incorporated by reference in its entirety.

BACKGROUND

Compared to vaginal births, cesarean deliveries (C-sections) increase the risk of complications for the mother and create a greater financial burden on the payor. Accordingly, vaginal births are often preferred unless certain health risks during labor warrant a C-section. Traditionally, the fetal heart rate and the mother's uterine activity are electronically monitored as labor progresses, and a physician manually categorizes fetal heart rate and uterine activity strips as one of three categories developed by the National Institute of Child Health and Human Development (NICHD) to determine whether a C-section delivery is appropriate. Category I strips are considered low-risk, and no intervention is typically required. At the other side of the spectrum, strips that persist at category III are considered high-risk, and preventive action (often a C-section) is typically required. Anything between category I and III is classified as a category II strip. Because the criteria for categorizing a strip at either extreme (i.e., category I or III) are stringent, over half of strips persist in category II where it is difficult to determine if intervention is required. Accordingly, it is often difficult for physicians to determine whether to recommend a C-section, resulting in unnecessary C-sections that increase the health risks to the mother.

SUMMARY

Systems, methods and computer-readable media are provided for predicting the neonatal vitality of infants that are likely to be born in a future time interval based on monitored physiological variables of the maternal patient measured during labor and, in some instances, for providing a decision support tool to clinicians and caregivers for proceeding with different delivery methods according to the predicted vitality scores. In particular, a fetal monitoring decision support system is provided for determining a likely neonatal score for an infant that is anticipated to be delivered within a future time interval. Embodiments of the disclosure described herein may provide a neonatal vitality score (such as APGAR score) that will represent the likely condition of an infant that will be delivered within a time horizon comprising a future time interval. Multiple neonatal vitality scores may be forecasted for different future time intervals and, in some embodiments, based on different delivery methods (e.g., vaginal delivery and C-section).

Aspects described herein include a fetal monitoring decision support system that forecasts vitality of a future infant by monitoring physiological variables during labor. In exemplary aspects, measurements for mother's uterine activity (UA) and the fetus's heart rate (FHR) are acquired over time. These measurements form a time series that can be used with predictive models trained to predict a neonatal vitality score indicating the likely health level of an infant anticipated to be born within a future time interval.

The fetal monitoring decision support system may use a plurality of models to forecast neonatal vitality scores for infants anticipated to be delivered within multiple different future time intervals. Additionally, different scores may be provided for different delivery methods, including vaginal delivery and a C-section. Using the maternal patient's dilation, a likely future time interval for a vaginal delivery may be determined, and a neonatal vitality score for a vaginal birth within the time interval may be compared with one or more thresholds and/or with a neonatal vitality score for a C-section delivery. In this way, caregivers can more accurately determine whether the fetus is in distress in labor in a way that will impact the health of the newly born infant and respond in accordance with the determinations. For instance, a notification may be provided with one or more of the forecasted neonatal vitality scores, and in some embodiments, a recommendation to proceed with a C-section or to increase monitoring of the patient in labor may be made based on the score. Accordingly, one aim of embodiments of this disclosure is to improve upon conventional industry practice by deriving accurate predictive capabilities for fetal monitoring to provide more effective treatment and care during labor and delivery. In this way, current embodiments provide for a counter-conventional technological solution that is unknown in the industry and the area of clinical support.

BRIEF DESCRIPTION OF THE DRAWINGS

The present invention is described in detail below with reference to the attached drawing figures, wherein.

DETAILED DESCRIPTION

Figure 1A:
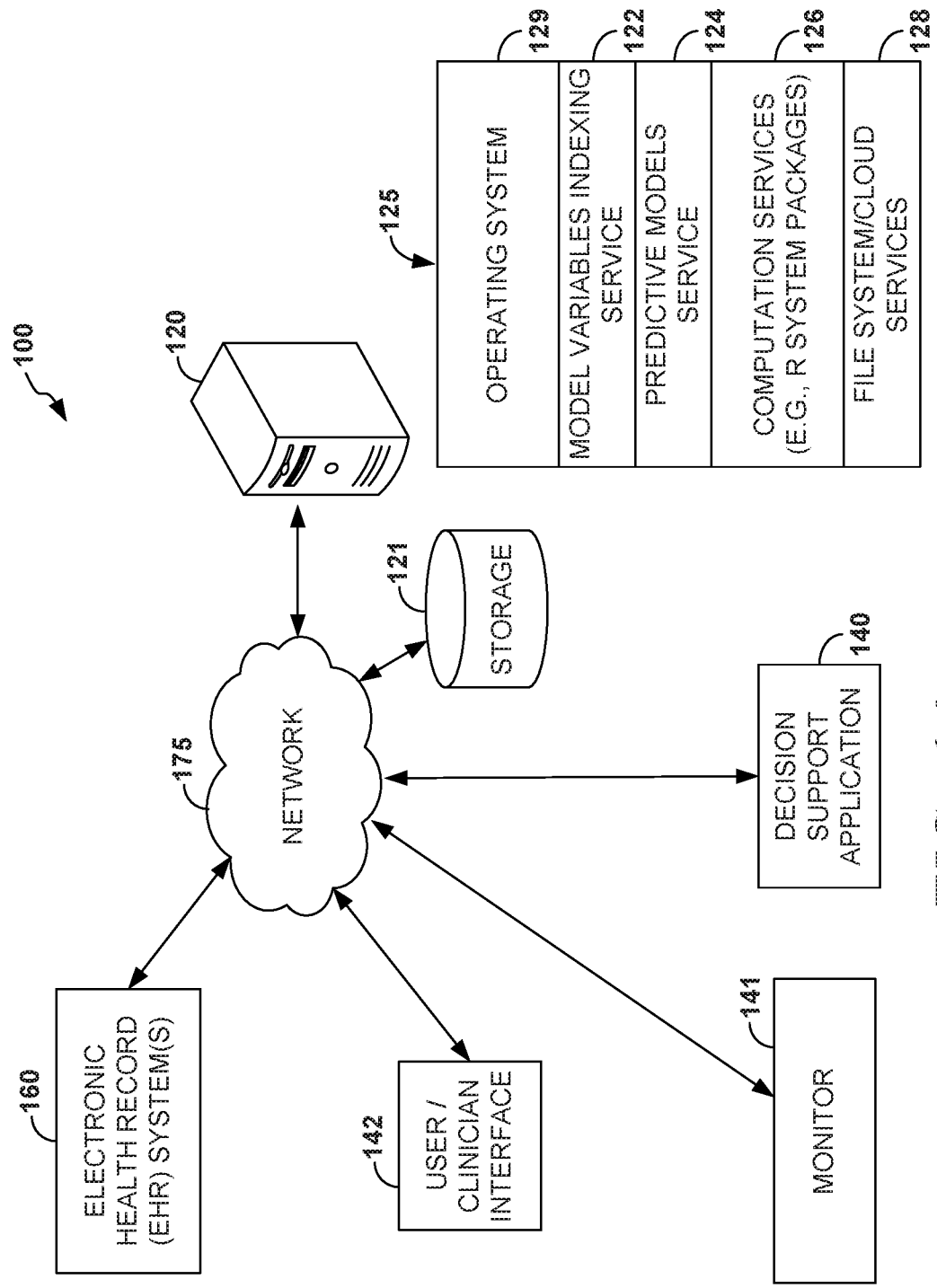
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, this disclosure describes, among other things, methods and systems for predicting neonatal vitality scores for an infant anticipated to be born within a future time interval based on fetal monitoring during labor. In some embodiments, the methods and systems may be implemented as a decision support computer application or tool and may be part of a more comprehensive healthcare decision support application for monitoring patients in labor and providing decision support to caregivers. Such decision support technology plays an important part of modern medicine.

Embodiments of the disclosure include systems, methods and computer-readable media for predicting the neonatal vitality of infants that are likely to be born in a future time interval based on physiological variables measured during labor. In particular, the fetal monitoring decision support system may provide forecasts of vitality of a future infant by monitoring physiological variables during labor. In exemplary aspects, measurements for mother's uterine activity (UA) and the fetus's heart rate (FHR) are acquired during labor, and UA and FHR time series are formed. These time series may be used to train and then utilize predictive models to forecast the neonatal vitality score for an infant that is anticipated to be delivered within a future time interval. The neonatal vitality score is a health level of an infant that is traditionally measured after delivery. For example, a neonatal vitality score may be an APGAR score, a cord blood gas measurement, or a combination thereof. Unlike with conventional methods, however, APGAR scores and cord blood gas measurements may be predicted for an infant who is not yet born by monitoring fetal and maternal vital signs during delivery.

In aspects described herein, the UA time series is used to identify the timing of contractions. Accelerations and/or decelerations of the FHR may be detected from the FHR time series, and FHR patterns may be identified (and classified) using at least classifications of decelerations, which may depend, in part, on the timing of the deceleration relative to identified contractions. Additionally, short-term and long-term variability metrics of the FHR may be computed and used to forecast the likely neonatal vitality score.

Multiple neonatal vitality scores may be predicted for the fetus (which may also be referred to as the fetal patient). The different scores may be specific to a future time interval and/or delivery method. For instance, delivery may either be a vaginal delivery or cesarean (C-section) delivery. Each type of delivery may have multiple neonatal vitality scores based on different future time intervals. For instance, some embodiments generate eight neonatal vitality scores for a vaginal delivery for eight different future time intervals ranging from 30 minutes to 10 hours and generate two neonatal vitality scores for a C-section delivery within a 30-minute and a one-hour future time interval.

Based on the plurality of neonatal vitality scores forecasted, a response may be initiated. The particular response may depend on a comparison of the neonatal vitality scores to threshold scores and/or to other forecasted neonatal vitality scores for the patient. Specifically, in some embodiments, one or more scores forecasted for vaginal delivery may be compared to a threshold to determine whether the fetus is likely in distress. If so, the neonatal vitality score may be compared to a neonatal vitality score for a C-section delivery to determine whether a C-section delivery would be a safer treatment course than a vaginal delivery. In other words, one or more predictive models may use data from active labor to forecast the health of a fetus upon delivery, and forecasts for vaginal delivery based on expected time-to-delivery may be compared with a forecast for cesarean delivery in the next hour. A response based on the forecasts may comprise initiation of a notification of the neonatal vitality scores, recommendations for modification of a care plan, such as increased monitoring and/or changing the delivery method, scheduling resources relating to a recommended modification of a care plan, and the like.

Accordingly, embodiments of the technology described herein improve on conventional medical decision support technologies by utilizing these innovated forecasting techniques and, thus, provide a practical application in decision support systems for monitoring and treating patients in labor, including aiding in determining an appropriate delivery method. Specifically, with respect to delivery methods, there has been an increasing trend in the rate of C-section deliveries over the past two decades. According to the Centers for Disease Control and Prevention, the overall C-section delivery rate in the United States increased from 20.7% in 1996 to 32.9% in 2009. While some efforts have been made to reduce the rate of non-medically indicated C-sections (which may be referred to herein as elective C-sections), the overall rate for C-sections was still at 32.2% in 2014. C-sections come with a number of adverse health risks, especially for the mother. Cesarean deliveries increase the risk of operative complications, and the risk of maternal mortality is doubled after C-sections. Further complicating the issue is that many expectant mothers who have previously had a C-section will require one for subsequent deliveries, and studies have confirmed that the increase in C-sections is partially due to subsequent deliveries of mothers who previously had a C-section. Mothers who have had previous C-sections, however, face increased health risks as it has been shown that the risk of placenta accreta, uterine rupture, and hysterectomy increase with each subsequent C-section.

In addition to the increased health risks, unnecessary C-sections increase the financial burden for payers, organizations, and individuals. For instance, a study released by the Center for Healthcare Quality and Payment Reform in 2013 indicated that reducing the cesarean delivery rate to the 15% recommended by the World Health Organization would save approximately $5 billion. The same study shows that the average cost of a C-Section for commercially insured patients is approximately 50% more than a vaginal birth—$27,866 per C-sections vs. $18,329 per vaginal birth. Similarly, Medicaid programs pay an average for $4,000 more per C-section. Accordingly, reducing unnecessary C-sections would not only reduce unnecessary health risks but also help to alleviate financial burden for payers.

Currently, healthcare decisions regarding the whether a C-section is appropriate are made using a three-tier classification system developed by the National Institute of Child Health and Human Development (NICHD). Using the conventional system, a healthcare provider views fetal heart rate strips and classifies the strips into one of three categories: normal (Category I), indeterminate (Category II), or abnormal (Category III). Category I strips are considered low-risk, and no intervention is typically required. At the other side of the spectrum, category III strips are considered high-risk and typically require preventive action (i.e., a C-section). Category II strips are between category I and category II strips and indicate that a C-section may be warranted. Because NICHD's criteria for categorizing a strip at either extreme (i.e., category I or III) are stringent and category II strips account for everything in between, over half of strips persist in being labeled category II where it is difficult to determine if intervention is required.

Accordingly, one aim of embodiments of this disclosure is to improve upon conventional industry technology by deriving more accurate predictive capabilities for fetal monitoring to provide more effective treatment and care during labor and delivery. Specifically, these forecasted neonatal vitality scores derived at least in part from physiological measurements, such as UA and FHR measurements, offer an innovative fetal monitoring decision support system because it provides an objective manner for determining fetal distress and/or proceeding with delivery. Specifically, at least one way that embodiments described herein improve upon conventional technology is because they are not vulnerable to inconsistent reliability between different caregivers interpreting the fetal monitoring strips and or even within the same caregiver. With more objective scoring utilizing forecasted neonatal vitality levels to determine fetal distress, embodiments described herein provide a more accurate approach for recognizing actual or potential fetal distress and decision support for the delivery. Embodiments help to alleviate problems arising from conventional system with too many strips being labeled as category II, which does not indicate a clear care plan for proceeding with the delivery.

Referring now to the drawings generally and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for forecasting neonatal vitality at a future time using the fetal heart rate and uterine activity during labor. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or more EHR systems, such as hospital EHR systems, health information exchange EHR systems, ambulatory clinic EHR systems, psychiatry/neurology EHR systems. Such EHR systems may be implemented in computer system 120. Similarly, EHR system 160 may perform functions for two or more of the EHR systems (not shown).

Network 175 may comprise the Internet, and/or one or more public networks, private networks, other communications networks such as a cellular network, or similar network for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which the likelihood(s) of delivering an infant with predicted vitality levels are determined according to the embodiments presented herein. Embodiments of user/clinician interface 142 also facilitate accessing and receiving information from a user or healthcare provider about a specific patient or population of patients including patient history; healthcare resource data; physiological variables (e.g., vital signs) measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders for the patient from the clinician/user based on the results of monitoring and predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems or other computing device(s) such as computing system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, patient decision support application 140 sends a recommendation or notification (such as an alarm or other indication) directly to user/clinician interface 142 through network 175. In an embodiment, application 140 sends a maintenance indication to user/clinician interface 142. In some embodiments, application 140 includes or is incorporated into a computerized decision support tool, as described herein. Further, some embodiments of application 140 utilize user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or health care provider about a specific patient, a set of patients, or a population according to the embodiments presented herein. Such information may include historical data; health care resource data; variables measurements, time series, and predictions (including plotting or displaying the determined outcome and/or issuing an alert) described herein; or other health-related information, and facilitates the display of results, recommendations, or orders, for example. In an embodiment, application 140 also facilitates receiving orders, staffing scheduling, or queries from a user, based on the results of monitoring and/or forecasted outputs, which may in some embodiments utilize user interface 142. Decision support application 140 may also be used for providing diagnostic services or evaluation of the performance of various embodiments. As shown in example environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment of monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables.

In one embodiment, monitor 141 comprises sensors for obtaining (and, in some instances, pre-processing or interpreting) and recording of maternal vital signs and fetal vital signs, which may be obtained continuously, periodically, or at irregular intervals. For example, in an embodiment, monitor 141 comprises a patient monitoring system for acquiring fetal heart rate (FHR) measurements and uterine activity (UA) measurements. In some embodiments, monitor 141 comprises a patient bedside monitor. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about the patient, such as the monitored variables and/or clinical narratives regarding the patient, used according to the embodiment of the invention disclosed herein may be received from a patient's historical data in EHR system 160, or from human measurements, human observations, or automatically determined by sensors in proximity to the patient.

Examples of physiological variables monitored by monitor 141 can include vital signs variables, such as maternal heart rate (bradycardia and tachycardia), fetal heart rate (bradycardia and tachycardia), blood pressure, uterine pressure, and respiratory rate, as described herein. Additionally, in some embodiments, monitor 141 may monitor other vital signs or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient to facilitate clinical decision making. In an embodiment, monitor 141 comprises a sensor probe, such as an EEG probe, and a communication link that periodically transmits identification information and probe data to decision support application 140 so that the time series of monitored values is stored and accessed by application 140, enabling application 140 to form an alarm indication and/or a physiological variable decision statistic. In an embodiment, application 140 facilitates the collection of raw sensor information, which may be received from monitor 141, and performs signal processing and computations thereby forming a physiological variable decision statistic, cumulative summing, trending, wavelet processing, thresholding, computational processing of decision statistics, logical processing of decision statistics, pre-processing or signal condition, etc., part or all of which may be performed on monitor 141, application 140, and/or computer system 120.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device comprising a sensor, application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or the computer system supporting application 140 for performing signal conditioning of the measured patient variable(s). In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or decision support application 140 operate in conjunction with software stack 125.

In embodiments, model variables indexing service 122 provide services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126.

Predictive models service 124 is generally responsible for providing one or more models for predicting neonatal vitality at future time intervals based on physiological variables monitored for a patient in labor as described in connection to method 200 of FIG. 2.

Computation services 126 perform statistical software operations, such as computing the FHR variability metrics as described herein. In an embodiment, computation services 126 and predictive models service 124 include computer software services or computer program routines. Computation services 126 also may include natural language processing services (not shown) such as Discern nCode™ developed by Cerner Corporation, or similar services. In an embodiment, computation services 126 include the services or routines that may be embodied as one or more software agents or computer software routines. Computation services 126 also may include services or routines for utilizing one or more models, including logistic models, for predicting neonatal vitality scores, such as the models described in connection to FIGS. 2-9.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner Healthe Intent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer-storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
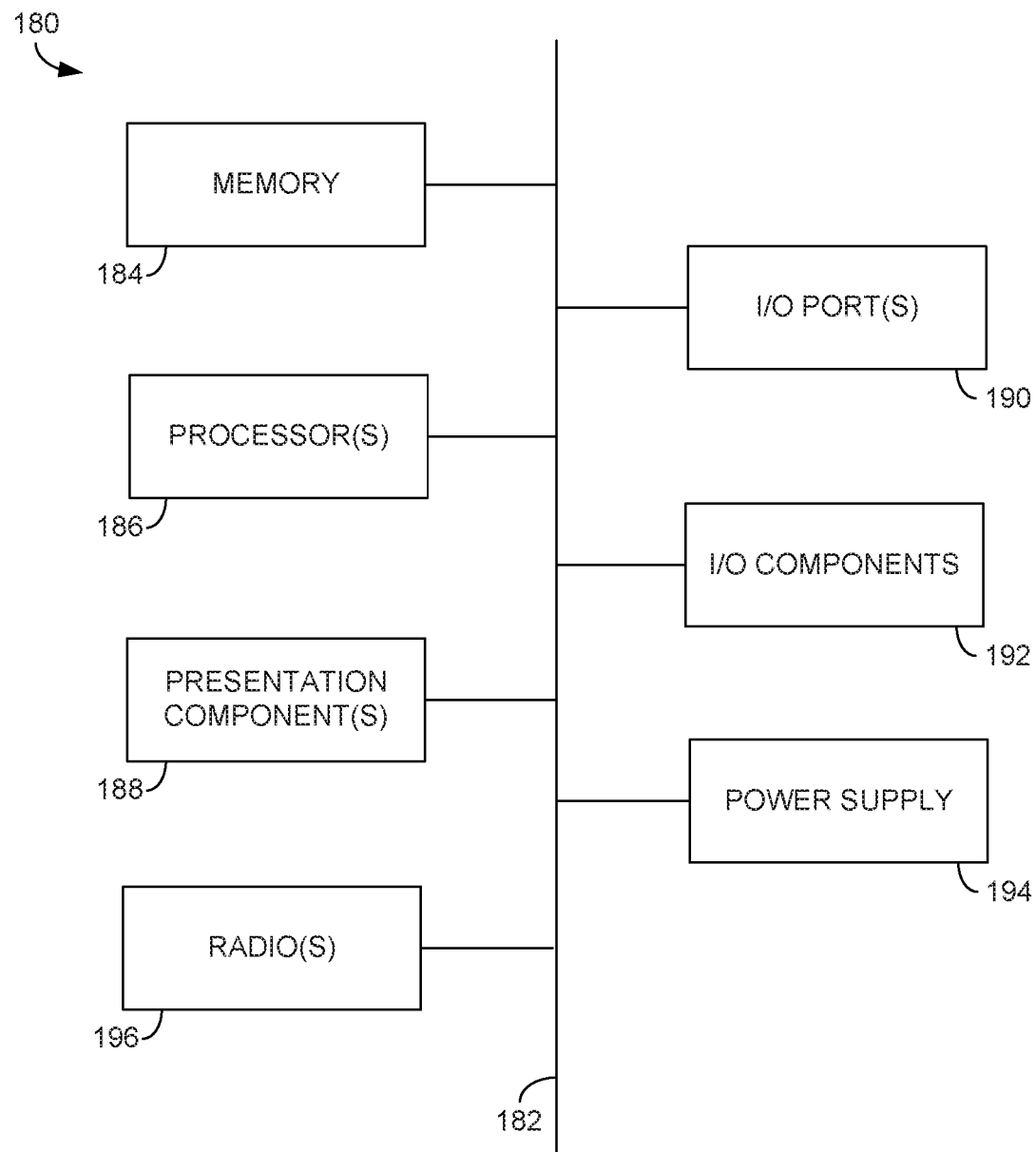

Turning briefly to FIG. 1B, there is shown one example embodiment of computing system 180 representative of a system architecture that is suitable for computer systems such as computer system 120. Computing device 180 includes a bus 182 that directly or indirectly couples the following devices: memory 184, one or more processors 186, one or more presentation components 188, input/output (I/O) ports 190, input/output components 192, radio 196, and an illustrative power supply 194. Bus 182 represents what may be one or more busses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1A is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 184 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 184 or I/O components 192. Presentation component(s) 188 present data indications to a user or other device. Exemplary presentation components include a display device, speaker, printing component, vibrating component, etc.

In some embodiments, computing system 196 comprises radio(s) 196 that facilitates communication with a wireless-telecommunications network. Illustrative wireless telecommunications technologies include CDMA, GPRS, TDMA, GSM, and the like. Radio 196 may additionally or alternatively facilitate other types of wireless communications including Wi-Fi, WiMAX, LTE, or other VoIP communications. As can be appreciated, in various embodiments, radio 196 can be configured to support multiple technologies and/or multiple radios can be utilized to support multiple technologies.

I/O ports 190 allow computing system 180 to be logically coupled to other devices, including I/O components 192, some of which may be built in. Illustrative components include a microphone, joystick, game pad, satellite dish, scanner, printer, wireless device, etc. The I/O components 192 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment. includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
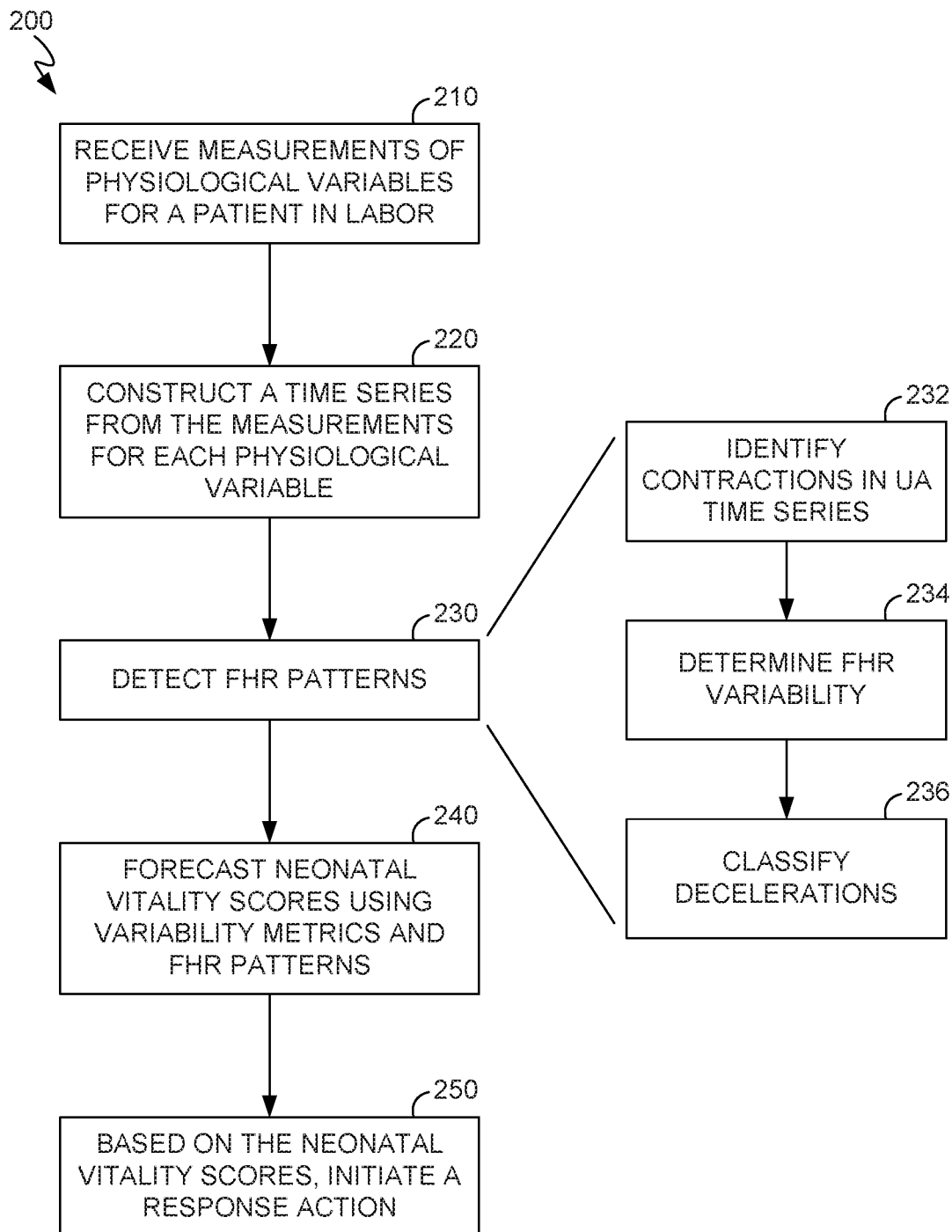
FIG. 2 depicts a flow diagram of a method for predicting vitality scores using measurements from the patient acquired during labor and suitable for implementation in a decision support system, in accordance with an embodiment of the disclosure.

Turning now to FIG. 2, an example embodiment of a method for predicting neonatal vitality at one or more future time intervals is provided and is referred to generally as method 200. In particular, example method 200 utilizes FHR patterns and variability for predicting the health of an infant within a time-to-birth interval. In some embodiments, method 200 is suitable for implementation as a computer-performed decision support tool or application for fetal monitoring and, thus, care plans for proceeding with a delivery based on more objective and accurate indicators of fetal distress than conventional technology would otherwise allow.

With reference to FIG. 2 and method 200, generally, the method 200 of providing decision support during labor and delivery by predicting neonatal vitality at one or more future time intervals for a delivery method is provided. First, at step 210, a plurality of measurements of physiological variables for a patient is received. The plurality of measurements may have been acquired for the patient over a period of time while the patient is in labor. In exemplary aspects, the physiological variables include fetal heart rate (FHR) and uterine activity (UA). In exemplary aspects, there may be two FHR feeds recording fetal heart rate in bpm. The UA variable may be recorded using either internal monitoring devices or external monitoring devices. For internal monitoring devices, UA may be measured as uterine pressure, while external monitoring devices may provide indications of UA through skin tension measurements. In exemplary aspects, UA is measured as uterine pressure using an internal monitoring device, which does not require the additional re-calibration based on the maternal patient's body mass index that is often involved with external monitoring devices. Additionally, in some embodiments, additional physiological variables are monitored and received. For instance, the patient's heart rate (i.e., maternal heart rate), the patient's level of dilation, patient's age, fetal gestational age, cord blood pH, and the like.

The measurements for the physiological variables may be received from the patient's EHR, such as a medical EHR within EHR system 160 in FIG. 1, or other data storage, or may be received directly from a monitoring device, such as patient monitor 141. In some aspects, the physiological variables are being monitored independently of the neonatal vitality forecasting system. In other words, rather than require additional monitoring to perform method 200, method 200 may leverage data that is often already being recorded in the normal course of monitoring a patient in labor, such as FHR and UA. Embodiments of step 210 may acquire the physiological variable measurements continuously, periodically, or at non-regular intervals. In some embodiments, the date/time information for each measurement is stored with the measured variable values.

Next, as step 220, a time series is constructed for one or more of the physiological variables measured. The time series may be constructed by appending the most recent physiological variable measurements to the historical measurements, using the associated date/time information. In some embodiments, the historical measurements comprise measurements obtained within a recent timeframe such as the previous 20 minutes, hour, or several hours. In such embodiments, only historical measurements from within this recent timeframe are retrieved and used for the constructing time series. In some aspects, the time series is evaluated to determine whether it is of sufficient length. In one embodiment, where the time series is determined to be greater than a pre-determined length, method 200 proceeds to step 230. But if the time series is not long enough, then method 200 returns to step 210, where additional measurements may be acquired. In one embodiment, the pre-determined length comprises at least 15 minutes.

In some aspects in which data is received from multiple FHR feeds for a single patient, constructing a time series includes selecting one or more FHR feeds from which data is used to predict neonatal vitality. In some aspects, for each time stamp, each of FHR 1 feed, FHR 2 feed, UA feed, and the maternal heart rate feed produce a sequence of four readings that are averaged to determine the arithmetic mean. The two FHR feeds may include indicators describing the type of monitoring devices being used, which may be used to determine which of the FHR feeds to rely. An example observation is provided below:
"ClinicalTime":"2016-07-09T14:55:53.841-05:00",
"FetalData":[{"Feed":"FHR1","Mode":"ULTRASOUND", "Values":"135,135,135,135" },
{"Feed":"FHR2", "Mode": "NO TRANSDUCER","Values":"0,0,0,0" } ],
"MaternalData":{"Feed":"Maternal","Mode":"EXTERNAL","Values":"0,0,0,0" }
"UAData":{"Feed":"UA","Values":"11,11,11,11" }.

It will be appreciated that data observations may be collected and stored in other formats.

In some instances, such as the one in Example 1, only one of the FHR feeds records an actual value in bpm, while the other feed only records 0's. Where only one FHR feed is recording, the values from the recording FHR feed are the values that are used. In some embodiments, when both feeds are recording, the two FHR feeds are combined into a single time series. In the instances in which both FHR feeds are recording data from monitoring devices having distinct indicators, the data is chosen from the more reliable source. In exemplary aspects, direct electrocardiogram (DECG) FHR feeds are chosen as more reliable over ultrasound FHR feeds, which are generally chosen as more reliable over "NO TRANSDUCER" sources. When both feeds are recording and their monitoring device indicators match (i.e., they are coming from the same type of source), one of the feeds may be determined as showing impossibly low values, such as an FHR of five bpm, while the other reading is reasonable. Accordingly, when both FHR feeds are active with matching indicators, the maximum of the two FHR values for each time stamp is taken. As used herein, FHR data may refer to a time series formed by one FHR feeds or both feeds.

Figure 3:
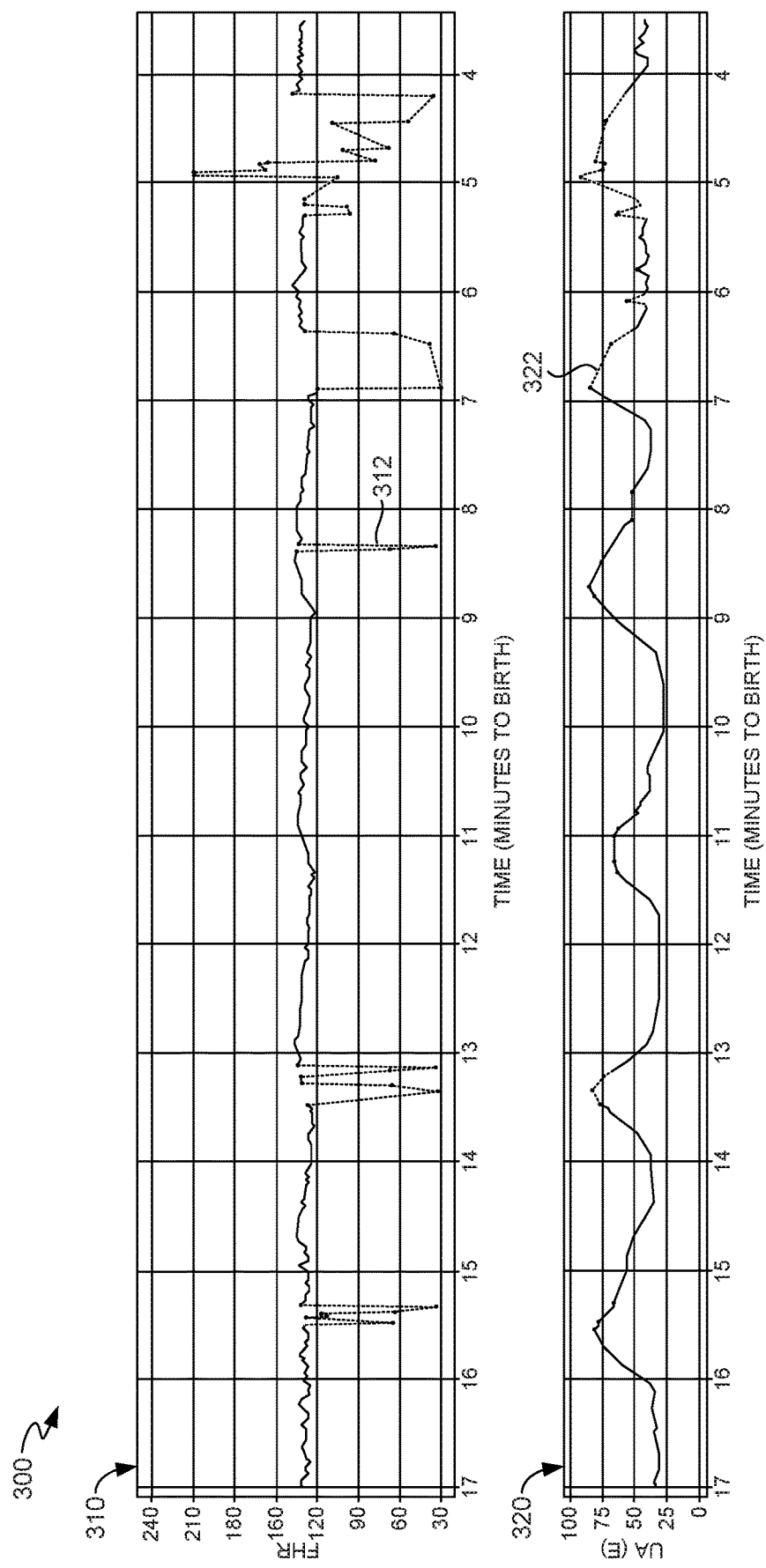
FIG. 3 depicts example fetal monitoring strips with artifacts identified in accordance with an embodiment of the disclosure.

In exemplary aspects, forming a time series in method 200 further comprises pre-processing the data to remove artifacts and/or address missing data, as shown in FIG. 3. FIG. 3 illustrates example fetal monitoring strips 300 that comprise a FHR time series strip 310 based on fetal measurements from the patient and a UA time series strip 320 based on maternal measurements of the patient. The FHR time series strip 310 depicts FHR measurements (measurement in beats per minutes) in time until birth, and UA time series strip 320 depicts UA measurements (in mmHg) in time until birth. As illustrated, the example FHR time series strip 310 includes one or more artifacts, including the spike 312 around 8 minutes and 20 seconds prior to birth, and the UA time series strip 320 includes missing gaps, such as the gap 322 at approximately 6 minutes and 50 seconds prior to birth. The artifacts and gaps are displayed as dashed lines in the example fetal monitoring strips 300 in FIG. 3.

Missing data may arise when one or more of the devices (e.g., a fetal monitoring device or a maternal monitoring device) is either not powered on or is on but not properly attached to the patient, which results in 0's being recorded. Because methods utilize both UA and FHR data during the same time series, observations in which one or both of these feeds are not recording properly (i.e., when the feeds are producing 0's) cannot be used and, therefore, are removed.

Removing the observations from non-recording creates a gap in the data. In some embodiments, when there is a gap between observations that is 60 seconds or longer in length, the data is separated into distinct segments to be analyzed separately, and any segment that less than 15 minutes long is removed from the time series. Segments with gaps less than 60 seconds may be retained, and interpolated values for those gaps may be used. For example, FIG. 3 shows dashed lines to account for gaps, such as gap 322, that are retained in the time series 320.

Further, in some aspects, processing the data into different segments is based on the type of maternal monitoring devices for each UA data point. In some embodiments, there are three possible indicators for the maternal monitoring device: internal, external, or "NO TRANSDUCER." As previously mentioned, internal monitoring devices record UA in terms of pressure, and, as such, a physical unit (e.g., mmHg) is associated with the observations. External devices typically measure skin tension and do not produce observations associated with a physical unit. External devices typically require calibration each time they are used because readings from external devices may vary between patients (particularly based on patient BMI) and may also vary within the same patient encounter if the calibration changes. Because of this, readings from external devices generally only have meaning relative to other observations from the same device with the same calibration. Due to the differences between external and internal maternal monitoring devices, segments of data from different devices may be analyzed separately, and segments of data from external devices with different calibrations may further be analyzed separately. To account for a change of device (or calibration), a segment may be split into two distinct pieces anytime the maternal monitoring device changes for more than 10 seconds. As previously mentioned, in some embodiments, only segments with a duration of at least 15 minutes are retained.

In addition to gaps, artifacts in the time series may be detected and removed. FIG. 3, for instance, depicts several artifacts, including the sharp drop in FHR around 8 minutes and 20 seconds prior to birth indicated by spike 312. These sudden drops are not indicative of the true FHR but, rather, are "artifacts" of true observations. Artifacts like spike 312 and the other artifacts shown in dashed lines in the FHR time series strip 310 in FIG. 3 may be caused by the patient coughing or movement of the fetal monitor.

In example embodiments, the Porto system is used to automate the artifact identification and imputation process. In accordance with the Porto system, a stable stretch of an FHR tracing, such as the tracing in the FHR time series strip 310, is one in which five consecutive observations have differences of less than 5 bpm. If the change in FHR between any two observations is greater than 20 bpm, it is identified as an artifact. Whenever a difference of 20 bpm is detected, a linear interpolation is applied between the first of these two observations and the first observation in the next stable stretch. In addition to artifacts occurring in the middle of an FHR tracing, the beginning and end of segments may have artificial observations that may be attributed to the monitoring device recording while it is still being positioned or removed. Accordingly, in example aspects, observations before the first stable segment or after the last stable segment are removed to ensure the data being analyzed is of a sufficient quality.

Although artifacts are only illustrated in the FHR time series strip 310 in FIG. 3, a similar process may be used to remove artifacts from the UA time series strip 320 if any artifacts are identified. In some aspects, for UA times series strips, observations are removed and replaced with interpolated values when the difference between any two consecutive observations is greater than or equal to 10 units, such as 10 mmHg, where the maternal monitoring device is an internal device. A stable segment for UA data may be one in which there are five consecutive values having differences of less than 5 units. For both FHR and UA time series, a portion of the time series may be discarded if the delay between an artifact and the next stable stretch is at least one minute.

Additionally, in some aspects, processing the data for the times series also includes imputing data to account for certain sampling delays. For instance, in some aspects, the exemplary sampling rate is a uniform rate of 1 second with no missing data. However, there may be larger gaps between observations caused by the sampling rate of the monitoring devices being set to a different rate due to other uses of the devices and data. Additionally, the sampling rates may be not uniform, which is common for fetal monitoring devices.

To achieve a sampling rate of 1 second, data may be imputed any time there is a delay greater than 1.5 seconds between consecutive samples. In this case, the number of imputed observations is determined to make the sampling rate as close to 1 second as possible. The imputed FHR values and UA values may be determined using Stine interpolation (for example, using the 'pracma' package in R), and noise may be added to the interpolated data. The added noise may be Gaussian with a mean of 0 and a standard deviation equal to the standard deviation of the observation values. Segments of data where no more than 20% of the data is imputed due to artifacts or missing values may be retained to form the time series.

Figure 4:
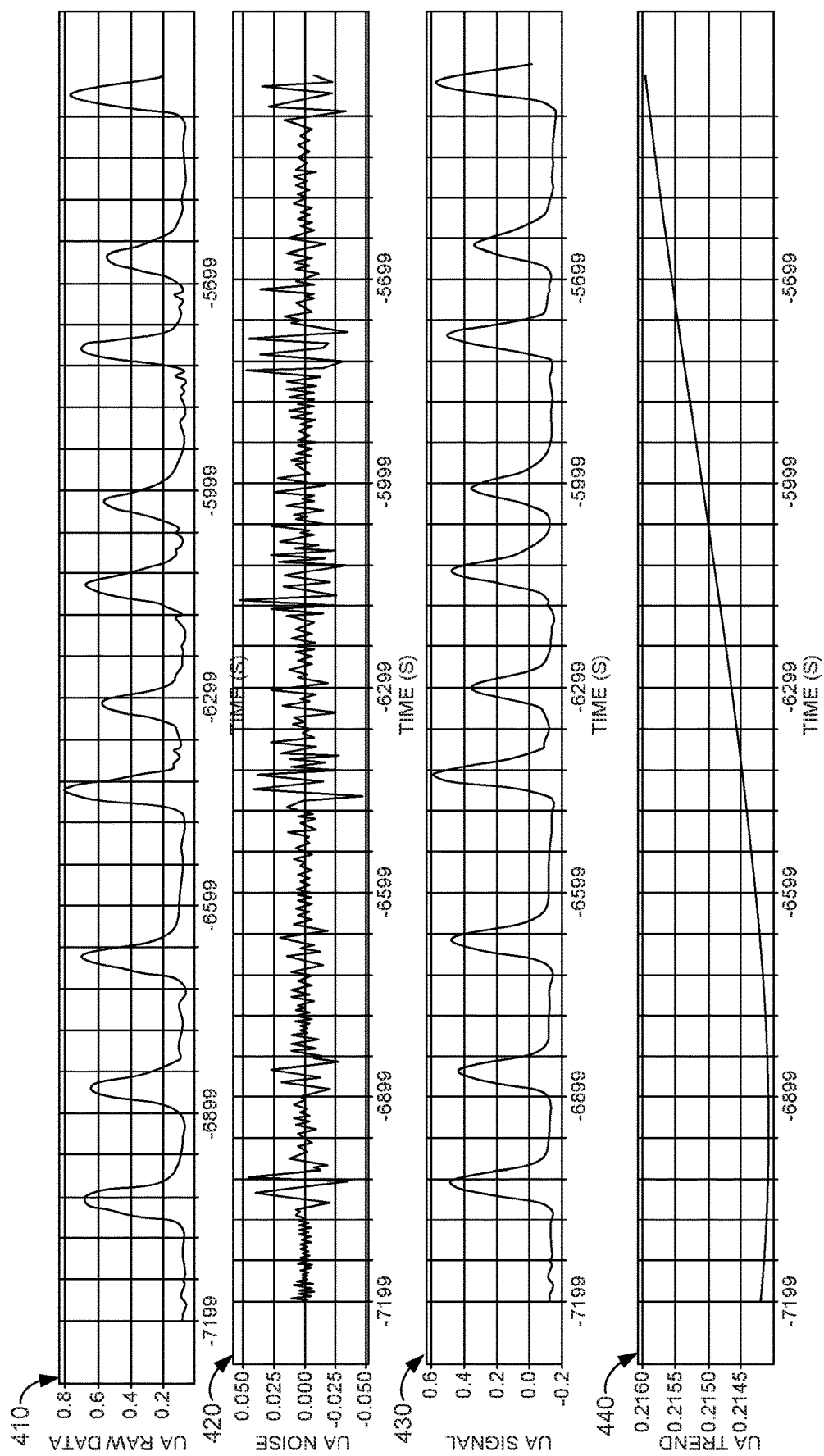
FIG. 4 depicts graphical illustrations of uterine activity sub-signals over time.
Figure 5:
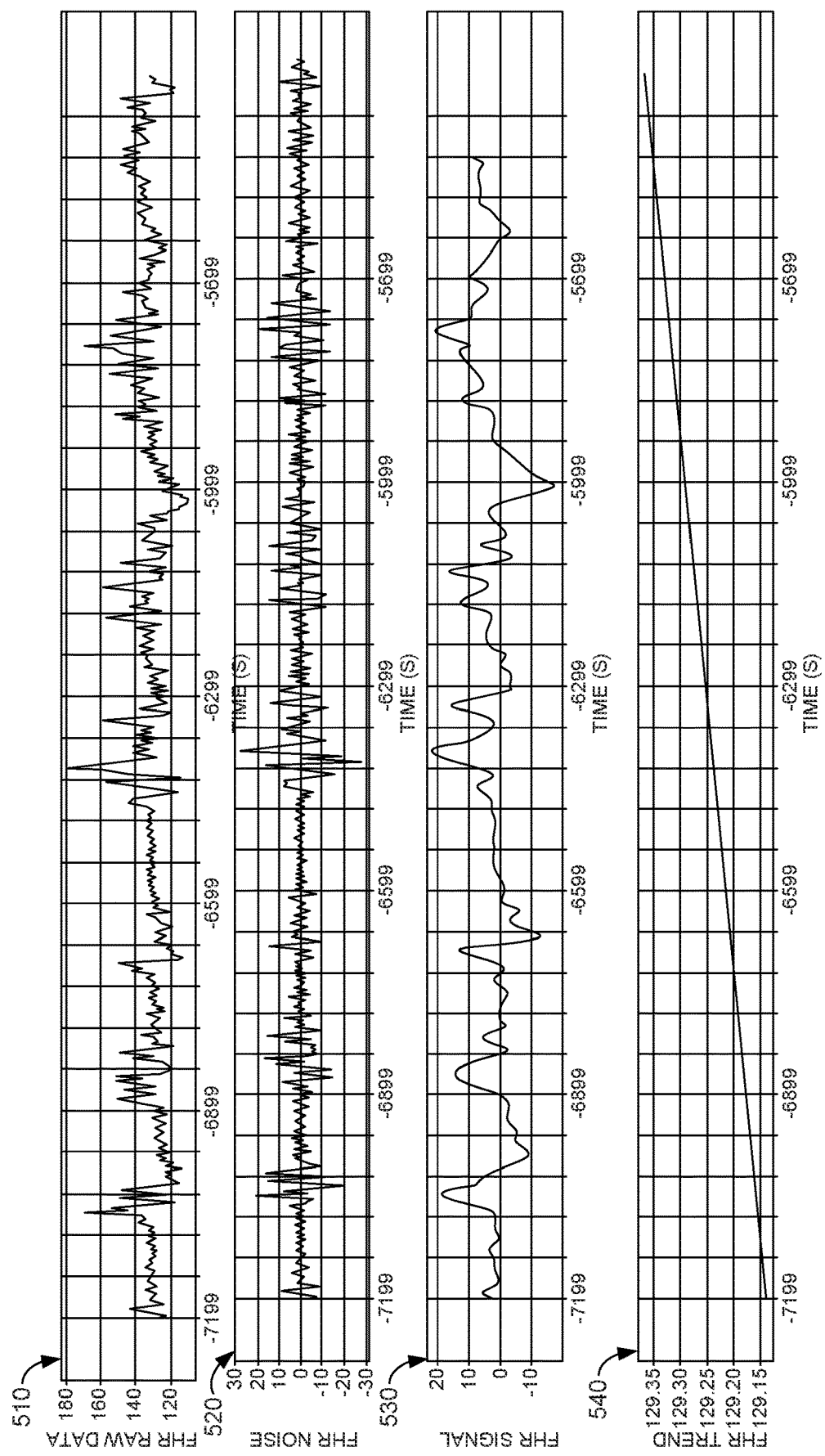
FIG. 5 depicts graphical illustrations of fetal heart rate sub-signals over time.

Further, in some embodiments, the time series data is filtered in the pre-processing stage. For example, the time series data for each variable may be filtered into three components: noise, signal, and trend. FIG. 4 illustrates a UA time series strip as it is broken down into components, which are also referred to herein as sub-signals. UA times series 410 represents the raw data time series that is traditionally what the healthcare provider is presented when monitoring a patient's UA. UA time series 410 is filtered into different components: UA component 420 representing the noise; UA component 430 representing the UA signal with a mean of 0; and UA component 440 representing the UA trend. The trend shown in UA component 440 is considered a (possibly nonlinear) long-term moving average. The two higher frequency components, UA component 420 and 430, each have a mean of zero such that the areas above and below the curves are equal and cancel each other out. The sum of the three components 420, 430, and 440 is equal to the full time UA series 410. The FHR time series may be similarly filtered as shown in the example FIG. 5. FHR time series 510 is the raw FHR data that is filtered into different components: FHR component 520 representing the noise; FHR component 530 representing the FHR signal with a mean of 0; and FHR component 540 representing the FHR trend.

In some aspects reduced to practice, Ensemble Empirical Mode Decomposition (EEMD) is used to filter the data using the 'Rlibeemd' package in R. Further, in other aspects, the base Empirical Mode Decomposition (EMD) may be used for filtering. The same processes may be used for filtering UA and FHR, but it is also contemplated each variable may be filtered differently. When using EEMD or EMD, the time series may be split into more than three components, such as 12 components, and one or more of the components may be summed together to create one of the components (sub signals) illustrated in FIGS. 4 and 5. For instance, in some aspects, UA component 420 for noise is a sum of five components identified using EMD, and UA component 430 is a sum of two or more components. FHR components may summed or aggregated in a similar fashion. In other embodiments, filtering may be performed using wavelet or spectral analysis.

By filtering, meaning can be attributed to the components of each variable times series (UA and FHR). For the FHR time series, the trend corresponds to a baseline heart rate of the fetus, the noise represents beat-to-beat variation (and perhaps some instrumental error), and the FHR signal (represented by FHR component 530) is the component forming the basis for FHR pattern detection to forecast neonatal vitality. In other words, the FHR component 530 represents de-noised deviation from the baseline (as shown by FHR component 540). In some embodiments, the UA component 420 representing noise is not used in the analysis, and the UA component 440 representing trend is effectively the minimum threshold that the UA must exceed to be categorized as a contraction, while the UA signal (i.e., UA component 430) is the oscillatory pattern analyzed to detect contractions.

Returning to method 200 of FIG. 2, at step 230, FHR patterns are detected. In exemplary aspects, such as method 200, FHR pattern detection comprises: identifying contractions from the UA times series (at step 232); determining FHR variability (at step 234); and classifying decelerations (at step 236).

Figure 6:
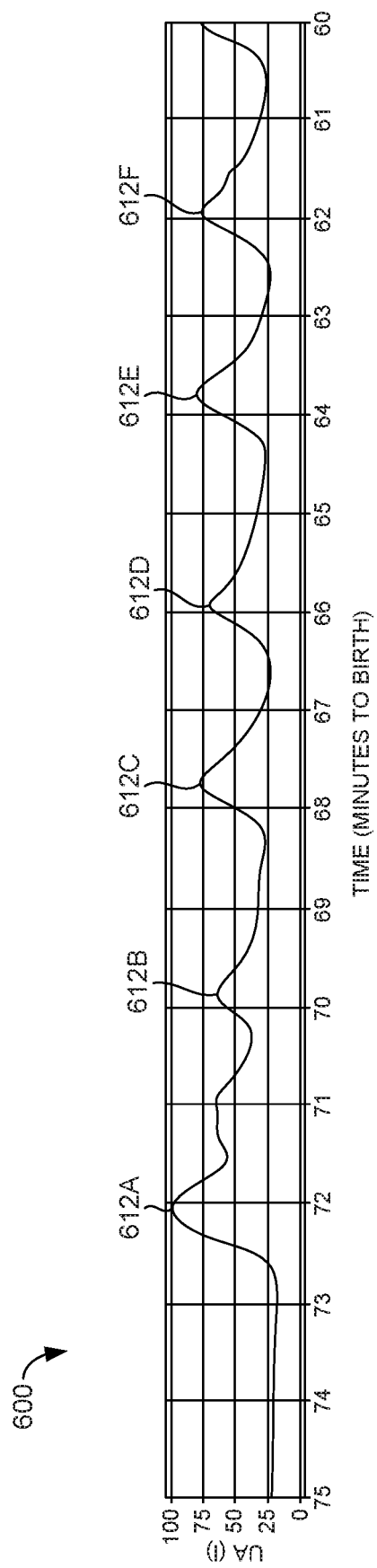
FIG. 6 depicts a graphical illustration of uterine activity signals over time to identify contractions in accordance with an embodiment of the disclosure.

Turning to FIG. 6, a UA time series strip 600 is depicted to illustrated a patient's contractions. In embodiments in which filtering is performed, the UA time series strip 600 may be a UA signal component that is a de-noised deviation from the baseline, similar to UA component 430 in FIG. 4. A contraction may be identified from the peaks in the UA time series strip 600. Specifically, identifying peaks includes identifying the largest local maxima for the UA time series 600 over a time interval. This identification process may involve several steps. Initially, identifying contractions may involve considering the local maxima of the UA signal that are positive. As previously discussed, the UA signal, may be determined from subtracting the noise (e.g., UA component 420 in FIG. 4) and the long-term trend (e.g., UA component 440 in FIG. 4) from the complete time series (e.g., UA times series strip 410 in FIG. 4). Because UA is roughly bounded by the interval [0,100], the long-term trend may be between 0 and 100, and the UA signal may oscillate (non-periodically) around 0. As such, positive values in the UA signal represent elevated activity. Any negative local maxima are likely either not contractions or are weak enough that they will have minimal effect on the FHR.

Next, after identifying positive local maximum, the largest local maximum within a time interval (i.e., a peak) is determined. In some embodiments, this time interval is 90 seconds. For instance, if a positive local maximum is identified at time $t_c$, the 90-second interval for determining the largest local maximum is $(t_c-45, t_c+45)$. In some embodiments, the timer interval may be a sliding window. Additionally, to account for elongated periods of elevated activity, the local maximum is a value that is at least one standard deviation above the mean UA over a pre-determined time interval, which in some aspects, is the one-minute interval preceding the maximum, i.e., $(t_c-60, t_c)$. Other measurements for defining the local maximum may be also used, such as one-half of a standard deviation above the mean UA. In FIG. 6, for instance, the UA time series strip 600 includes a plurality of identified contractions (peaks 612A-F) that occurred within 73 minutes until delivery.

In some aspects, the strength of the contraction is related to the depth and duration of a corresponding deceleration if one exists. When UA is measured from an external device, variable data forming the time series may be combined with the maternal patient's BMI to approximate actual contraction strength.

Continuing with detecting FHR patterns, at step 234, FHR variability metrics are computed. A FHR time series includes a baseline and will likely include accelerations and decelerations in which the FHR departs from the baseline by a threshold amount. Identification and, in some instance, classification of accelerations may be used to determine the FHR variability outside of the acceleration and deceleration segments. The FHR variability metrics may then be used for analyzing decelerations in conjunction with the contractions identified from the UA time series.

As used herein, FHR baseline refers to an approximation of the mean FHR data values during a specified time frame. In some embodiments, the FHR baseline comprises the mean FHR values within a 10-min window rounded to nearest 5 bpm. The FHR baseline may not take into account accelerations, decelerations, and periods with marked FHR variability. In some embodiments, determining the FHR baseline involves determining whether the time interval considered includes is a minimum length of identifiable segments that do not include accelerations, decelerations, and periods with marked FHR variability. In some instances, this minimum length is two minutes for a 10-minute time interval. Additionally, in some aspects, the two-minute interval does not necessarily need to be contiguous within the 10-minute interval. If the minimum length is not present, the segment may be considered indeterminate, and the previous 10-minute interval may be used for the FHR baseline.

Accelerations may be identified when there is an increase in FHR values with a peak FHR value above a threshold amount from the FHR baseline value for a threshold duration. In some embodiments, the threshold amount and/or threshold duration is dependent on the gestational age. For instance, when the gestational age is at least 32 weeks, an acceleration may be identified by an increase in FHR values with a peak at least 15 bpm above the FHR baseline value for a duration of at least 15 seconds, and for a gestational age less than 32 week, an acceleration may be identified when there is an increase in FHR values with peak at least 10 bpm above the baseline for a duration of at least 10 seconds.

For each acceleration detected, information relating to the acceleration may be logged and stored. In some embodiments, for example, each acceleration is logged with the following information: (i) onset time, which is defined as the time of the first observation with an FHR value above the FHR baseline; (ii) the time of the acceleration peak, which is defined as when the FHR values exceed a threshold value (such as 15 bpm) above the baseline; (iii) the slope between onset and peak; and (iv) duration of the acceleration, which is considered to be finished when the FHR returns to the baseline. Based on this information, the accelerations may be classified as abrupt, prolonged, or having or marked variability. In some embodiments, an abrupt acceleration is defined as an acceleration in which the time between onset and peak is less than or equal to 30 seconds. Alternatively or additionally, an abrupt acceleration may be defined as having a slope greater than 0.5. An acceleration with marked variability may be an abrupt acceleration with a slope of greater than 2. A prolonged acceleration may be defined as an acceleration with a duration of at least two minutes. In practice, a prolonged acceleration has a duration between two and ten minutes because durations over 10 minutes results in a change in FHR baseline.

After the accelerations are identified, FHR variability may be computed using segments of the FHR time series. FHR variability metrics may include long-term variability metrics and short-term variability metrics. In example embodiments, two long-term variability metrics are computed: (i) acceleration count within a pre-determined time interval; and (ii) and the Hurst exponent of the FHR time series over a pre-determined time interval. For instance, one long-term variability metric may be the number of accelerations in the 10-minute interval preceding a contraction. In aspects in which an acceleration is defined as 15 bpm above the baseline for a duration of least 15 seconds, this acceleration count may be referred to as 15×15 count over the 10-minute window. The second long-term variability metric may be the Hurst exponent of the FHR time series over the 20 minute interval preceding the contraction. In some embodiments, the pre-determined interval for computing the Hurst exponent is a minimum of five minutes prior to the start of the FHR time series segment. The Hurst component may be considered an aggregate of number of lags along the correlation and is used to determine self-similarity in the long term.

In some aspects, two short-term variability metrics are also computed: SDANN and RMSSD. SDANN, as used herein, refers to the standard deviation of time between heart beats (which may also be referred to as NN intervals) and may be computed in milliseconds. RMSSD, as used herein, is the root mean squared of successive deviations of NN intervals and also may be computed in milliseconds. SDANN and RMSDD provides measures of beat-to-beat variability. In some embodiments, SDANN and RMSSD are computed for segments with at least 120 observations within the 5-minute interval prior to the contraction, and, in some embodiments, the 120-observation minimum may be satisfied only after removing observations within accelerations and decelerations. When there are less than 120 qualifying (e.g., not accelerations and decelerations) observations in the five-minute interval, the time interval may be extended up to a maximum window interval, which may be ten minutes. In some embodiments, the short-term variability metrics (SDANN and RMSSD) are computed only if variability was not classified as marked when considering the accelerations. One or more of the metrics may be used to classify FHR variability. In one embodiment, for instance, the Hurst exponent, SDANN, and RMSSD are combined to classify variability as either absent, minimal, normal, or marked based on standard deviations away from the mean of the log-normal distribution from the data. At least some of the variability metrics may be computed using the FHR time series after excluding observations occurring within an acceleration or deceleration. For computing other variability metrics, such as the Hurst exponent, the acceleration and decelerations are not removed.

Continuing with detecting FHR patterns, decelerations (or the lack thereof) are analyzed and, where present, classified at step 236. Decelerations may be identified based on the time of a contraction identified from the UA time series. Where the peak of the contraction occurs at time $t_c$, the maximum FHR (relative to the baseline) in the time interval preceding the peak of the contraction is first determined. For instance, the time interval may be 40 seconds prior to the peak of contraction $[t_c-40, t_c]$. Upon identifying the maximum FHR during that 40-second interval, it is determined whether there is a drop in FHR that is a threshold distance below the previous maximum and a threshold distance below the FHR baseline, which is called the minimum threshold (MT). In exemplary embodiments, the threshold values are determined using the long-term variability metrics. Additionally, it is determined whether there is a recovery (i.e., a rise in FHR value following the identified drop) to at least either the previous maximum FHR or the FHR baseline.

When a decrease (drop) in FHR values that meets the threshold distances is identified, it is classified as natural variability based or a deceleration based on variability metrics, and, where it is a deceleration, the type of deceleration may be determined. When the FHR decrease is determined to be a deceleration (rather than natural variability), it may be categorized into a type of deceleration based on the (i) amplitude (magnitude of the decrease), (ii) the slope from onset to the nadir (the lowest FHR value), (iii) duration of the deceleration, and (iv) the timing relative to the contraction. In some aspects, the different types of decelerations are defined as follows:

Variable: amplitude $\geq 15$, slope $\leq -0.5$, and duration$\in[15 \text{ s}, 120 \text{ s}]$ Early: amplitude $\geq$MT, slope $>-0.5$, and occurs within 2 s of contraction Late: amplitude $\geq$MT, slope $>-0.5$, and occurs more than 2 s after contraction Prolonged: duration $>120$ s It is contemplated that variable, early, late, and prolonged decelerations may be defined in alternative ways. For instance, a variable deceleration may be defined as an abrupt decrease in FHR with less than 30 seconds between onset and nadir, a decrease of at least 15 bpm, and a duration between 15 seconds and 2 minutes. Early and late decelerations, on the other hand, may both be defined by a gradual decrease with at least 30 seconds between onset and nadir, but the nadir of a late deceleration occurs after the peak of contraction and a nadir of an early deceleration occurs at the same time as the peak of a contraction. Additionally, a prolonged deceleration may have a deceleration of at least 15 bpm lasting between 2 minutes and 10 minutes.

In accordance with the above definitions, it is possible for a deceleration to be classified as two types. Specifically, an early or late deceleration can also be classified as a prolonged deceleration. Additionally, decelerations, including a late or variable decelerations, may be determined by recurrent where the decelerations occur with at least half of the contractions in a pre-determined time interval, such as a 20-minute window, for example. Intermittent decelerations are referred to herein as decelerations that are not recurrent.

Generally, some level of decelerations are expected with a contraction; however, some deceleration patterns may be a concern to the patient's own health and/or the health of the fetus. Early decelerations, for instance, may indicate head compression, which is typically not a cause of concern, and variable decelerations may indicate potential issues, such as chord compression. Variability decelerations are not necessarily associated with a uterine contraction and, when they are, onset, depth, and duration may vary with successive contractions. Late decelerations may indicate fetal distress.

Figure 7:
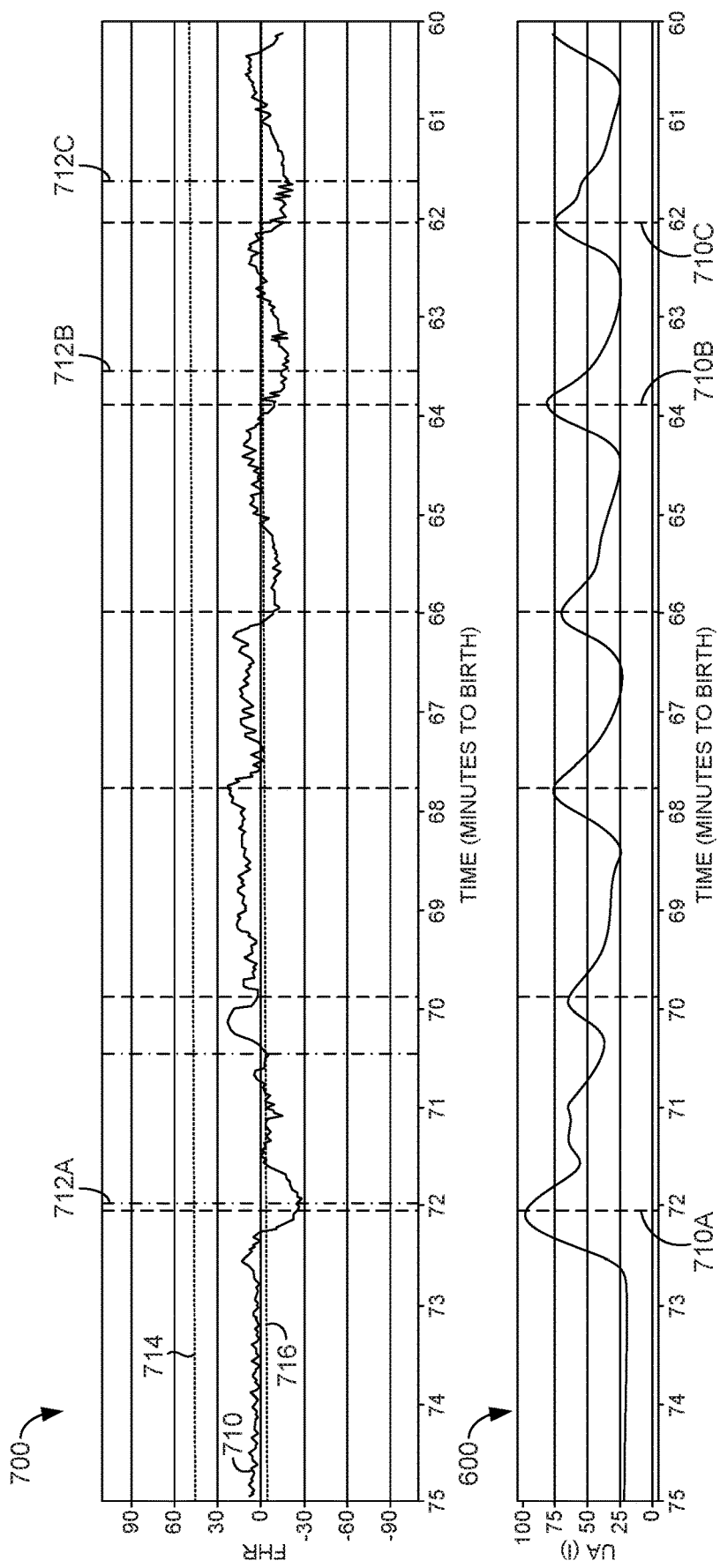
FIG. 7 depicts graphical illustrations of a fetal heart rate signal and uterine activity signal to illustrate FHR patterns in accordance with an embodiment of the disclosure.

Turning to FIG. 7, an example graphic user interface 700 with fetal monitoring strips are illustrated. The example fetal monitoring strips includes a FHR time series strip 700 and UA time series strip 600, which is the same UA time series strip 600 provided in FIG. 6. In example embodiments, the FHR time series strip 700 and UA time series strip 600 are presented to a caregiver, such as a physician, who is monitoring the patient. The strips 600 and 700 may be presented together as shown in the graphic user interface 700 in FIG. 7 such that the relationship between UA (contractions) and FHR (decelerations and other variability) can be visually perceived by the caregiver. Accordingly, as previously described, UA time series strip 600 depicts six identified contractions (identified as peaks 612A-F in FIG. 6), and contraction marks 710, shown as dashed vertical lines extend through each contraction peak in the UA times series strip 600. Contraction marks 710 also extend into the FHR time series strip 700 to indicate the time at which the contractions are occurring within the FHR time series strip 700.

In addition to contraction marks 710, the FHR time series strip 700 may include deceleration marks 712 marking times of FHR decelerations. In the example graphic user interface 700 of FIG. 7, the deceleration marks 712 are shown as dotted vertical lines. While the contraction marks 710 and deceleration marks 712 are shown as dashed and dotted vertical lines in FIG. 7, it may be appreciated that other types of markings, such as lines of different colors, symbols, or a combination thereof, may be used to denote contractions and decelerations.

As shown in FIG. 7, decelerations or variability in the FHR may occur near a contraction identified from the UA time series 600. For instance, deceleration mark 712A occurs within approximately two seconds of the peak of the contraction 710A. Based on the definitions for deceleration discussed with respect to step 236 of method 200, mark 712A may represent an early and/or variable FHR deceleration. Additionally, decelerations depicted with deceleration marks 712B and 712C occur over two seconds after contractions designated by contraction marks 710B and 710C, respectively. The time at which deceleration 712B occurs may reflect a transition between a category I and a category II fetal monitoring strips, which may prompt additional or increased monitoring. In accordance with embodiments of method 200, decelerations indicated by marks 712B and 712C may be determined to be late decelerations. As certain deceleration types are more indicative of fetal distress (such as late decelerations), the different decelerations types may be depicted within the graphic user interface with visually distinct markings, such as markings of different colors.

While decelerations are often associated with contractions, some variable decelerations occur independently of contractions. Accordingly, in addition to identifying and classifying decelerations resulting from an identified contraction, some embodiments involve detecting decelerations that fit criteria for a deceleration between a previous contraction and the current contraction and then validating whether any variable decelerations have been detected. This process helps to account for these spontaneous variable decelerations when determining the FHR variability and computing short-term metrics. In some embodiments, searching for these spontaneous variable decelerations may depend on the frequency of contractions. Specifically, spontaneous variable decelerations are searched for only when contractions are not happening with a sufficient frequency. In an embodiment, for example, when no contractions are detected between updates of the forecasting model, which may occur every two to five minutes, the system searches for spontaneous variable decelerations.

Figure 8:
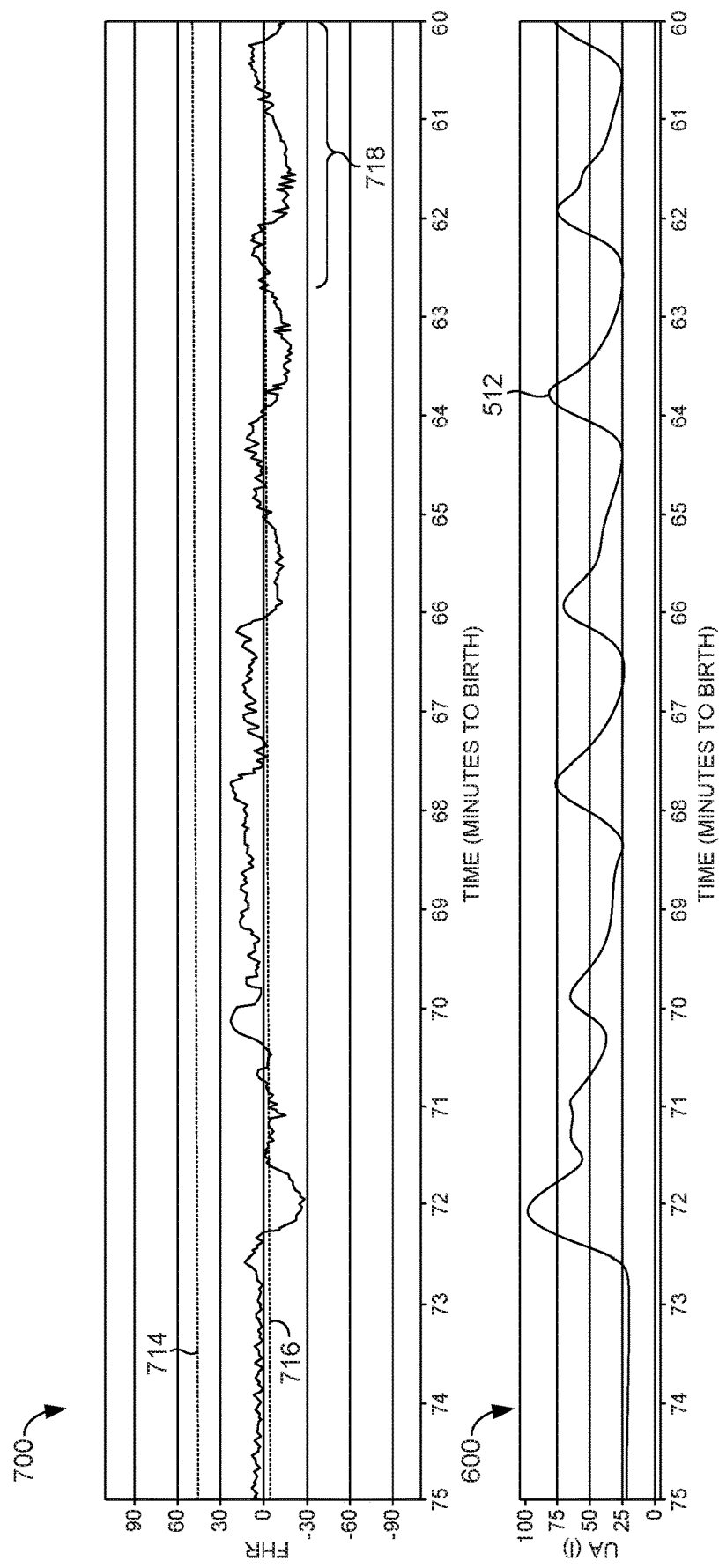
FIG. 8 depicts graphical illustrations of a fetal heart rate signal and uterine activity signal to illustrate tachycardia and bradycardia in accordance with an embodiment of the disclosure.

In addition to FHR patterns based on decelerations, embodiments of the disclosure involve identifying any instances of tachycardia and bradycardia using the FHR baseline. Turning to FIG. 8, example FHR time series strip 700 and UA time series strip 600 from FIG. 7 are provided. Similar to FIG. 7, the FHR time series strip 700 is presented with indicators for tachycardia and bradycardia boundaries. For instance, horizontal line 714 may represent tachycardia while horizontal line 716 indicates bradycardia. As used herein, bradycardia is present where the FHR baseline is less than 100 bpm, and tachycardia is present where the FHR baseline is greater than 160 bpm. In some aspects, adjustments to determinations of tachycardia and bradycardia are made based on an estimated gestational age. For instance, bradycardia may be present when the FHR baseline is less 110 bpm depending on gestational age. In FIG. 8, the stretch of FHR values 718 appear to be borderline bradycardia. As shown in FIG. 7, horizontal lines 714 and 716 may be displayed within graphic user interface 700 with the contraction marks 710 and deceleration marks 712 such that a user can quickly observe the detection of tachycardia/bradycardia. The borderline bradycardia 718 may also be an indication of a switch from category I to category II strips. It is contemplated that the presence or absence of bradycardia and tachycardia may be done before, after, or contemporaneously with detection and classification of decelerations in accordance with embodiments of method 200.

Additionally, it may be determined whether the FHR time series is sinusoidal. In some aspects, this determination is made by performing a spectral analysis. A determination that the FHR time series is sinusoidal may occur when the maximal spectral power occurs at a pre-determined frequency. In some embodiments, this frequency is between 0.091-0.044 Hz, which is a range that includes the frequencies typically associated with dangerous sinusoidal patterns while allowing for the presence of some noise. A dangerous sinusoidal pattern may include a pattern of one oscillation every 12-20 seconds.

At step 240 of FIG. 2, neonatal vitality scores may be forecasted using the detected FHR patterns detected and the calculated variability metrics. In exemplary embodiments, the neonatal vitality scores are predicted in terms of a 1-minute APGAR score and/or a 5-minute APGAR score. In other embodiments, a 10-minute APGAR score and/or a 20-minute APGAR score may be provided. APGAR scores are used as measurement for a new infant's health and have traditionally been determined after birth based on appearance (color), pulse (heart rate), grimace (reflex), activity (muscle tone), and respiration (breathing rate/effort). APGAR scores may range from 0 to 10. A normal APGAR score is greater than or equal to 7, while low APGAR scores are those less than 7 and indicate potential issues with the infant's health. In some aspects, low APGAR scores are considered those between 6 and 3, while scores less than 3 are considered critical. In some embodiments, a neonatal vitality score is provided as a forecasted cord blood gas measurement (also referred to as cord blood pH), which provides an objective measurement. Further, in some aspects, the neonatal vitality score is a combination of an APGAR score and a cord blood gas measurement.

In accordance with embodiments of the disclosure, one or more neonatal vitality scores, such as APGAR scores, may be predicted. The neonatal vitality scores may be a numerical score, such as a numerical APGAR score, a cord blood gas measurement, or a percentage of vitality, or may be a qualitative score, such as healthy, normal, critical, low, and the like. In some embodiments, the forecasted scores are included only for a vaginal delivery within future time intervals, and, in other embodiments, the forecasted scores may include scores for vaginal delivery and C-section. In this way, recommendations for proceeding with a planned vaginal delivery be made by using scores for each delivery time. Neonatal vitality scores may be predicted after the start of active labor and forecasted for one or more future time intervals.

The neonatal vitality scores are forecasted using a predictive model with the patient's FHR and UA measurements as input. Specifically, FHR patterns and variability metrics from the FHR and UA time series may be used with the model to generate the neonatal vitality scores. FHR patterns over time may be aggregated and input into the one or more predictive models. The particular predictive model(s) utilized may be specific to a delivery type and future time interval such that scores for each delivery method and future time interval may be determined using separate models. Example predictive models that may be used include but are not limited to: moving average, exponential smoothing, autoregressive moving average, autoregressive integrated moving average, trend estimation, linear regression, nonlinear regression, and a statistical classification model, such as for example, logistic regression, support vector machines, neural networks, cluster algorithms, binomial classification models, multinomial classification models, and decision tree (e.g., random forest) models. In an example reduced to practice, least absolute shrinkage and selection operator (LASSO) models were used.

Additionally, the neonatal vitality forecast model be based on a spectral analysis. For instance, in an embodiment reduced to practice, spectral power was computed in a running 2-minute time window and relative spectral density in non-overlapping bands were compared. The three non-overlapping bands were considered: low-frequency (⅟30-⅟15 Hz), mid-frequency (⅟15-⅖15 Hz), and high-frequency (⅖15-1 Hz). In particular, the normalized high-frequency power (nHF), normalized mid-frequency power (nMF), and mid-frequency to high-frequency ratio (MFHF) were computed in accordance with the following definitions:

$$nMF = \frac{MF}{LF + MF + HF} \times 100$$

$$nHF = \frac{HF}{LF + MF + HF} \times 100$$

$$HFMF = \frac{MF}{HF}$$

where LF, MF, HF are the sums of the spectral powers for frequencies in the respective intervals. The means of each (nMF, nHF, MFHF) are computed for each of the pre-determined intervals before birth. Changes in spectral density may be tracked as labor progresses.

The forecast model(s) uses a plurality of features to predict the neonatal vitality score, such as an APGAR score. The features used may include:
- Type of maternal (UA) monitoring device;
- Duration of observations;
- Number of contractions and the approximate period of contractions;
- Number of each type of deceleration: early, late, prolonged, and variable (with or without contraction separately);
- Maximum number of consecutive late or prolonged decelerations;
- Recurrence of late and variable decelerations;
- Number of prolonged and abrupt accelerations;
- NICHD variability classification: absent, minimal, marked, or sinusoidal;
- Bradycardia or Tachycardia;
- NICHD Category: at start of interval, at end of interval, averaged over the interval, and maximal category;
- Mean short-term variability metrics: SDANN, RMSSD;
- Mean Hurst exponent;
- Maximum power and associated frequency;
- Mean spectral metrics: nMF, nHF, MFHF;
- Correlation between strength of contraction and depth/duration of decelerations; and
- Demographic, medical, and clinical data (including medial history) of the mother, such as diagnoses, labs, procedures, and/or medications.

When training the models to predict neonatal vitality, additional metadata may be provided. This metadata may include the delivery outcome, the delivery method, the patient's age, the patient's BMI, the gestational age of the fetus, actual cord blood pH (also referred to as blood gas pH), time to delivery, dilation, and certain medications taken by the patient. In this way, the model may also be trained to take into consideration the patient's age, gestational age, patient's BMI, and medications.

As previously mentioned, the forecasts for neonatal vitality are provided for a delivery (either vaginal or cesarean) within a future time interval. For forecasts of neonatal vitality based on a C-section delivery, the score may be provided with the assumption that the C-section would occur within a shorter time period. For instance, the neonatal vitality score may be based on a C-section occurring within one hour or 30 minutes from the time of the forecasts. Accordingly, in some embodiments, scores for a C-section birth are provided for both a one-hour interval and a 30-minute interval. Because the timing for vaginal births are much more variable and can be predicted less easily, neonatal scores for vaginal deliveries may be generated for a greater number of time intervals. For instance, in some embodiments, eight neonatal vitality scores for vaginal births are forecasted for the following time-to-birth intervals (in hours):
- (10, 7)
- (7, 5)
- (5, 4)
- (4, 3)
- (3, 2)
- (2, 1)
- (1, 0.5)
- (0.5, 0)

In an embodiment reduced to practice, LASSO regression models (e.g., cv.glmnet with alpha=1) were used to generate each forecast for the time intervals/delivery method combinations. The system included eight models for vaginal births (for the above eight time intervals), and two models for cesarean births (for the two shortest time intervals), for a total of ten models. The models were trained with different combinations of approximately 3 to 14 features chosen from the features list discussed herein. The area under the curve (AUC) for the models ranged from 0.792 to 1.0, with the eight out of ten models having an AUC of 0.9 or greater.

Based on the neonatal vitality scores, a response action may be initiated, as shown at step 250 of FIG. 2. The response action may be based on a comparison of one or more of the neonatal vitality scores to a threshold score and/or a comparison of neonatal scores for different delivery methods. One such response action may be a recommendation or notification that is emitted or otherwise communicated to a caregiver responsible for the patient's care, such as an obstetrician. For instance, when the neonatal scores for vaginal deliveries satisfy a threshold indicating that a significant risk of a low or critical APGAR score exists, a notification of the risk may be generated and communicated via a bedside alarm, user/clinician interface (such as interface 142 described in FIG. 1A), or may be communicated to a smartphone or personal computing device of a caregiver, thereby alerting the caregiver of a potential risk through continued labor. In one embodiment, the notification comprises an event signal and includes one or more neonatal vitality scores. Additionally, some embodiments of step 250 may comprise storing the result of the determination of neonatal vitality scores in an EHR associated with the patient and further may include providing the patient's EHR (or facilitating access to the EHR) in the notification. In some embodiments, the threshold risk level for neonatal vitality scores based on vaginal delivery is set by a user/clinician.

In addition to or alternatively of the notification, a set of one or more actions relating to preventative and/or therapeutic responses may be initiated. For example, as described herein, when the scores for vaginal delivery fall below a threshold risk level, the neonatal vitality scores for a C-section may be presented and compared to the neonatal scores for a vaginal delivery to provide a recommendation regarding whether to proceed with a vaginal or C-section delivery. In some embodiments, scores for each of the time intervals are determined and provided to a clinician and the most likely time-to-birth interval for a vaginal delivery may be determined based on the patient's dilation and other factors, such as the number of previous deliveries the patient has had. The neonatal vitality score for a vaginal delivery within that most-likely time interval is then compared to the score for a C-section for a determination of whether to proceed with a C-section or have labor continue for a vaginal delivery.

Additionally, therapeutic responses may be initiated based on one or more of the predicted neonatal vitality scores. For example, a recommendation to increase patient monitoring or level of care, or administering a therapeutic intervention, such as a medication or procedure may be generated. The therapeutic response recommendation may be provided in conjunction with a notification of the predicted neonatal vitality scores, and/or may be provided via a user/clinician interface, such as interface 142, described in connection with FIG. 1A.

Yet another action that may be initiated comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the predicted neonatal vitality scores.

A further action that may be initiated based on the determined likelihood includes scheduling healthcare resources for the patient. For example in one embodiment, it may be determined based on the neonatal vitality scores that the patient should undergo a C-section within an hour and, based on this determination, an operating room (OR) resource may be automatically reserved for the patient, OR staff may be notified and/or automatically scheduled, and transportation/support staff or resources for getting the patient to the OR may be called. In one embodiment, this action comprises modifying or updating a resource/scheduling electronic record in a resource/scheduling system.

Many different arrangements of the various components depicted, as well as components not shown, are possible without departing from the spirit and scope of the present invention. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized system for providing a decision support tool, the computerized system comprising one or more processors and memory storing computer-usable instructions that, when executed by the one or more processors, cause implementation of operations comprising:
   receiving a plurality of measurements acquired over time for physiological variables for a patient in labor, the plurality of measurements comprising fetal heart rate (FHR) measurements and uterine activity (UA) measurements;
   detecting FHR patterns from the FHR measurements and the UA measurements;
   based on at least the FHR patterns, forecasting a plurality of predicted neonatal vitality scores, each predicted neonatal vitality score being for delivery occurring at a pre-defined future time interval, wherein the pre-defined future intervals for the plurality of predicted neonatal vitality scores are different; and
   based on the plurality of predicted neonatal vitality scores, initiating a response action.

2. The computerized system of claim 1, wherein detecting the FHR patterns comprises identifying contractions from the UA measurements and computing one or more FHR variability metrics from the FHR measurements.

3. The computerized system of claim 2, wherein the one or more FHR variability metrics comprises: acceleration count, Hurst exponent, standard deviation of beat-to-beat intervals, and root mean squared of successive deviations of beat-to-beat intervals.

4. The computerized system of claim 2, wherein the one or more FHR variability metrics comprises one or more short-term FHR variability metrics and one or more long-term FHR variability metrics.

5. The computerized system of claim 1, wherein detecting FHR patterns comprises detecting decelerations within the FHR measurements and classifying detected decelerations as one or more of variable, early, late, and prolonged.

6. The computerized system of claim 1, further comprising one or more sensors configured to acquire the measurements for UA from the patient in labor and one or more sensors configured to acquire the measurements for FHR from the patient in labor.

7. The computerized system of claim 1, wherein the plurality of predicted neonatal vitality scores comprise one or more of a predicted 1-minute APGAR score, a predicted 5-minutes APGAR score, and a predicted cord blood pH measurement.

8. The computerized system of claim 1, wherein the response action comprises automatically generating an electronic notification of fetal distress.

9. The computerized system of claim 1, further comprising a data store configured for storing and logging the FHR measurements, the UA measurements, and the plurality of predicted neonatal vitality scores for the patient.

10. The computerized system of claim 1, wherein the plurality of predicted neonatal vitality scores are forecasted using relative spectral density.

11. The computerized system of claim 1, wherein each predicted neonatal vitality score comprises either a normal APGAR score or a low APGAR score.

12. The computerized system of claim 1, wherein the plurality of predicted neonatal vitality scores includes at least one neonatal vitality score for vaginal delivery and at least one neonatal vitality score for cesarean delivery.

13. A method implemented by a computer software program operating on a computing system, the method comprising:
   receiving a plurality of measurements acquired over time for physiological variables for a patient in labor, the plurality of measurements comprising fetal heart rate (FHR) measurements and uterine activity (UA) measurements;
   detecting FHR patterns from the FHR measurements and the UA measurements;
   generating a plurality of predicted neonatal vitality scores based on at least the FHR patterns, the plurality of predicted neonatal vitality scores comprising one or more neonatal vitality scores predicted for vaginal delivery occurring within a pre-defined vaginal delivery future time interval and one or more neonatal vitality scores predicted for cesarean delivery occurring within a pre-defined cesarean delivery future time interval; and based on the plurality of predicted neonatal vitality scores, initiating a response action.

14. The method of claim 13, wherein the one or more neonatal vitality scores predicted for cesarean delivery comprise a neonatal vitality score predicted for cesarean delivery occurring within the next 30 minutes and a neonatal vitality score predicted for cesarean delivery occurring between the next 30 minutes and an hour.

15. The method of claim 13, wherein the one or more neonatal vitality scores predicted for vaginal delivery comprise a plurality of neonatal vitality scores predicted for vaginal delivery occurring within different pre-defined vaginal delivery future time intervals ranging from 30 minutes to 10 hours.

16. The method of claim 15, wherein the one or more neonatal vitality scores predicted for vaginal delivery includes eight neonatal vitality scores.

17. The method of claim 13, wherein each predicted neonatal vitality score is generated utilizing a separate predictive model.

18. The method of claim 13, wherein detecting the FHR patterns comprises computing one or more FHR variability metrics.

19. The method of claim 13, wherein detecting the FHR patterns comprises using a timeseries of the UA measurements to detect one or more decelerations in a timeseries of the FHR measurements.

20. A computer storage media having computer-executable instructions embodied thereon that, when executed by one or more processors, causes performance of operations for implementing a decision support system, the operations comprising:

receiving a plurality of measurements of physiological variables for a patient in labor, the plurality of measurements being acquired over a time span and comprising fetal heart rate (FHR) measurements and uterine activity (UA) measurements;

using the UA measurements and the FHR measurements, detecting FHR patterns, the FHR patterns including decelerations corresponding to uterine contractions;

generating a plurality of predicted neonatal vitality scores based on at least the FHR patterns, each predicted neonatal vitality score being for delivery occurring at a pre-defined future time interval, wherein the pre-defined future intervals for the plurality of predicted neonatal vitality scores are different; and based on the plurality of predicted neonatal vitality scores, initiating a response action.

21. The computer storage media of claim 20, wherein the plurality of predicted neonatal vitality scores includes at least one neonatal vitality score for vaginal delivery and at least one neonatal vitality score for cesarean delivery.

22. The computer storage media of claim 20, wherein each predicted neonatal vitality score comprises either a normal APGAR score or a low APGAR score.

23. The computer storage media of claim 20, wherein the plurality of predicted neonatal vitality scores comprise one or more of a predicted 1-minute APGAR score, a predicted 5-minutes APGAR score, and a predicted cord blood pH measurement.

24. The computer storage media of claim 20, wherein detecting the FHR patterns comprises identifying contractions from the UA measurements and computing one or more FHR variability metrics from the FHR measurements.

25. The computer storage media of claim 24, wherein the one or more FHR variability metrics comprises: acceleration count, Hurst exponent, standard deviation of beat-to-beat intervals, and root mean squared of successive deviations of beat-to-beat intervals.

26. The computer storage media of claim 24, wherein the one or more FHR variability metrics comprises one or more short-term FHR variability metrics and one or more long-term FHR variability metrics.

27. The computer storage media of claim 20, wherein detecting FHR patterns comprises detecting decelerations within the FHR measurements and classifying detected decelerations as one or more of variable, early, late, and prolonged.

28. The computer storage media of claim 20, wherein the operations further comprise acquiring the measurements for UA from the patient in labor via one or more sensors and acquiring the measurements for FHR from the patient in labor via the one or more sensors.

29. The computer storage media of claim 20, wherein the response action comprises automatically generating an electronic notification of fetal distress.

30. The computer storage media of claim 20, wherein the operations further comprise storing and logging the FHR measurements, the UA measurements, and the plurality of predicted neonatal vitality scores for the patient.

31. The computer storage media of claim 20, wherein the plurality of predicted neonatal vitality scores are forecasted using relative spectral density.

\* \* \* \* \*